US005439442A

United States Patent [19]
Bellifemine

[11] Patent Number: 5,439,442
[45] Date of Patent: Aug. 8, 1995

[54] DEVICE FOR MONITORING AND CONTROLLING AN INTRAVENOUS INFUSION SYSTEM

[76] Inventor: Francesco Bellifemine, Via Perla 57, Verese, Italy

[21] Appl. No.: 119,307

[22] Filed: Sep. 13, 1993

[30] Foreign Application Priority Data

Sep. 18, 1992 [IT] Italy ............... MI92A2153

[51] Int. Cl.$^6$ ............... A61M 5/16
[52] U.S. Cl. ............... 604/65
[58] Field of Search ........... 604/65, 67, 122, 246, 604/250–253; 128/DIG. 13

[56] References Cited

U.S. PATENT DOCUMENTS

| 3,197,068 | 7/1965 | Corbin et al. | 604/65 |
| 3,655,095 | 4/1972 | Kienitz . | |
| 4,137,940 | 2/1979 | Faisandier | 604/253 |
| 4,493,710 | 1/1985 | King et al. | 604/253 |
| 4,496,351 | 1/1985 | Hillel et al. | 604/250 |
| 4,509,943 | 4/1985 | Hanzawa . | |
| 4,533,350 | 8/1985 | Danby et al. . | |
| 4,623,331 | 11/1986 | Cewers et al. | 604/253 |
| 4,718,896 | 1/1988 | Arndt et al. | 604/253 |
| 4,909,786 | 3/1990 | Gijselhart et al. | 604/253 |
| 5,078,683 | 1/1992 | Sancoff et al. . | |
| 5,088,990 | 2/1992 | Hivale et al. | 604/253 |

FOREIGN PATENT DOCUMENTS

2272435 5/1974 France .
2331088 11/1975 France .
8403632 9/1984 WIPO .

Primary Examiner—John D. Yasko
Assistant Examiner—Manuel Mendez
Attorney, Agent, or Firm—Diller, Ramik & Wight

[57] ABSTRACT

A device for monitoring an intravenous infusion system is provided which includes a drip chamber for receiving droplets of liquid for intravenous infusion delivered thereto by a delivery tube with the drips being sensed through an associated droplet sensing, counting, comparing and responding circuit system. Three relatively movable jaws are provided, two of which are relatively preloaded by a spring which is locked but can be releases by a brief energization of an electromagnet to terminate liquid flow through the delivery tube.

20 Claims, 11 Drawing Sheets

DEVICE FOR MONITORING AND CONTROLLING AN INTRAVENOUS INFUSION SYSTEM

BACKGROUND OF THE INVENTION

This invention relates to a monitoring device for monitoring and controlling an intravenous infusion system.

Intravenous infusion systems currently have to be monitored by the nurse and/or patient to confirm that delivery is not interrupted, that complete emptying does not take place and that administration does not take place at a rate different from that prescribed for the medicament concerned. In the first case there would be an unwelcome lengthening of the administration time; in the second case blood would begin to rise up the tube because its pressure is no longer opposed by that of the drip liquid; in the third case delivery at a rate greater than that prescribed could have harmful consequences for the patient.

SUMMARY OF THE INVENTION

The object of the present invention is to obviate the aforesaid drawbacks by providing a monitoring device able to monitor and control an intravenous infusion system.

If a drip passage within a reservoir is interrupted, or if the level of the liquid contained in said reservoir falls depending on the particular case (type or position of the sensor element), the sensor element indirectly operates the warning element to draw attention, hence enabling the aforesaid problems to be obviated and/or corrected in good time.

More evolved embodiments of the device are able to control the delivery on the basis of preset values or halt it if it becomes dangerous for the patient by exceeding a predetermined value. The invention is illustrated by way of non-limiting example in the figures of the accompanying drawings.

DESCRIPTION OF THE PREFERRED EMBODIMENTS

Figure 1:
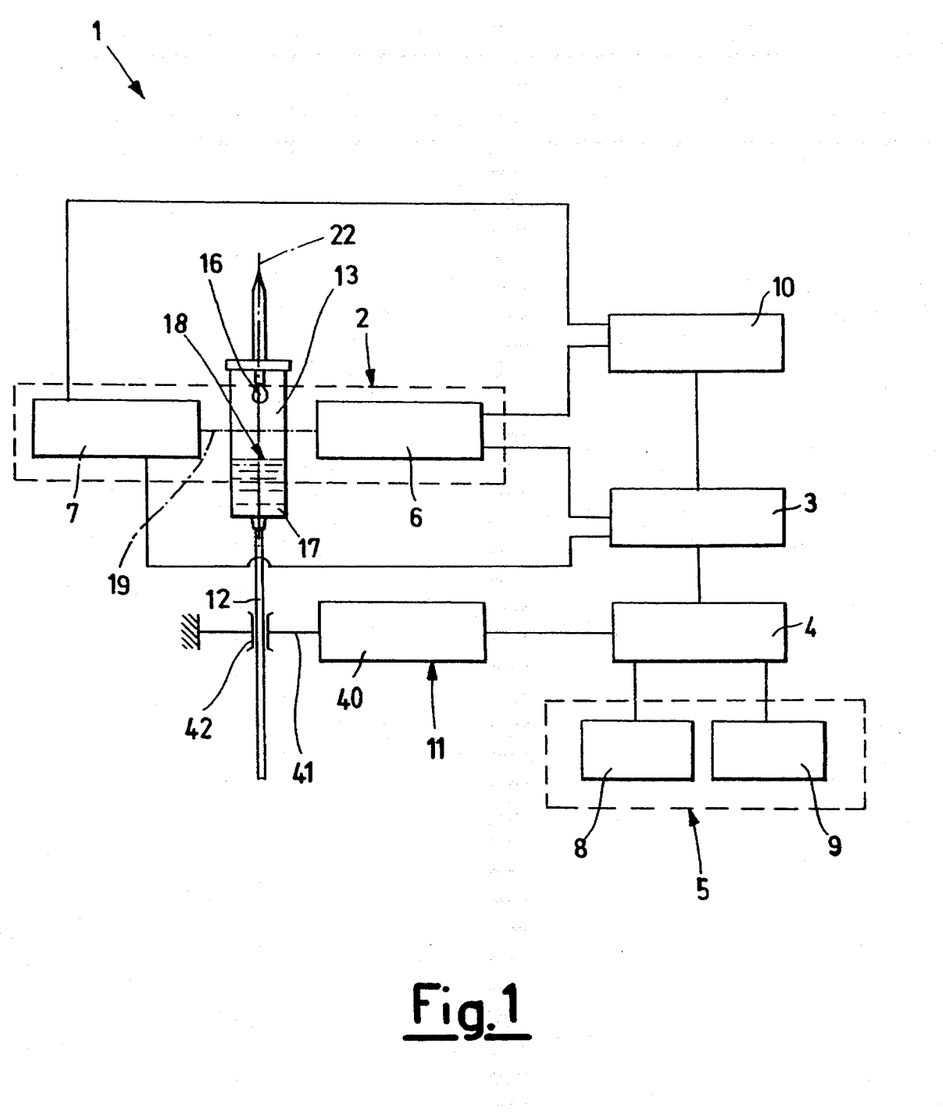
FIG. 1 is a schematic view of a device according to the invention showing a first embodiment of the electronic circuit, represented as a block diagram, and a first embodiment of a valving element.

With reference to the aforesaid figures and, in particular to FIG. 1, a monitoring device for monitoring an intravenous infusion system comprises substantially a sensor element 2, an element 3 for measuring time intervals, a relay 4, a warning element 5 and a power unit 10. In the illustrated embodiment the sensor element 2 comprises a photosensor formed from a transmitting portion 6 and a receiving portion 7. The receiving portion 7 is operationally connected to the time interval measurement element 3 which is connected to the relay 4 operating the warning element 5. In the illustrated embodiment the warning element 5 is both an acoustic and lighting warning element/possibly incorporating a remote calling device 9 (for example for automatically calling the nurse via cable or radio). The power unit 10 powers all the elements of the circuit 1 at low voltage.

In a more evolved embodiment the device 1 can also comprise a valving element 11 for a tube 12 positioned downstream of the drip chamber or reservoir 13 of the intravenous infusion system. In a first embodiment the valving element 11 is of the type comprising a first electromagnet 40 acting on a first slidable element 41 able to compress the tube 12 by deforming it against a fixed counteracting member 42. Further embodiments of the valving element 11 are described hereinafter. For practical reasons the sensor element 2 is housed (see for example FIGS. 2 and 4) within the jaws 14 of a gripper element 15 to be applied to the outside of the drip chamber or reservoir 13. On that side which adheres to the drip chamber 13 the gripper jaws 14 have a curvature with a radius less than the radius of the chamber of the smallest commercially available reservoirs. In this manner the gripper element 15 is always securely centered about the drip chamber 13 independently of its size.

The photosensor or sensor 2 can be of barrier type, reflection type, reflex type, infrared or modulated infrared type according to requirements. The sensor 2 need not, however, be of optical type, i,e., need not be a photosensor, but instead can be a capacitive proximity sensor.

All the aforementioned sensors can be housed in or associated with the gripper element 15 to allow it to be rapidly applied to the drip chamber 13. Depending on requirements or the operational characteristics of the sensor elements 2 the monitoring device 1, on application, can be made to detect the passage of the droplet 16 along its vertical trajectory or the presence or absence of the portion of liquid 17 in the reservoir 13 or the level of the surface 18 of said portion of liquid 17 within the chamber 13. In the first case (see the device shown in FIGS. 2 and 3), each time the droplet 16 crosses the axis 19 the time interval measuring element 3 begins to count time intervals from zero. If, after a total time interval of an extent predetermined on the basis of the type of medicament to be administered, there is no further passage of droplets 16 with corresponding zeroing of the measured time intervals, the time interval measuring element 3 operates the warning elements 5 and/or 9 via the relay 4, depending on how it is programmed. In the second and third case the time interval measuring element 3 immediately operates the relay 4 on disappearance of the portion of liquid 17 or the surface 18 respectively. In these cases no delay need be incorporated as it is obvious that the liquid is about to finish.

For constructional and applicational reasons the time interval measuring element 3, the relay 4, the warning element 5 and the power unit 10 can all be housed within the same housing 20 from which plug pins 21 emerge for plugging into a conventional electric socket.

Figure 2:
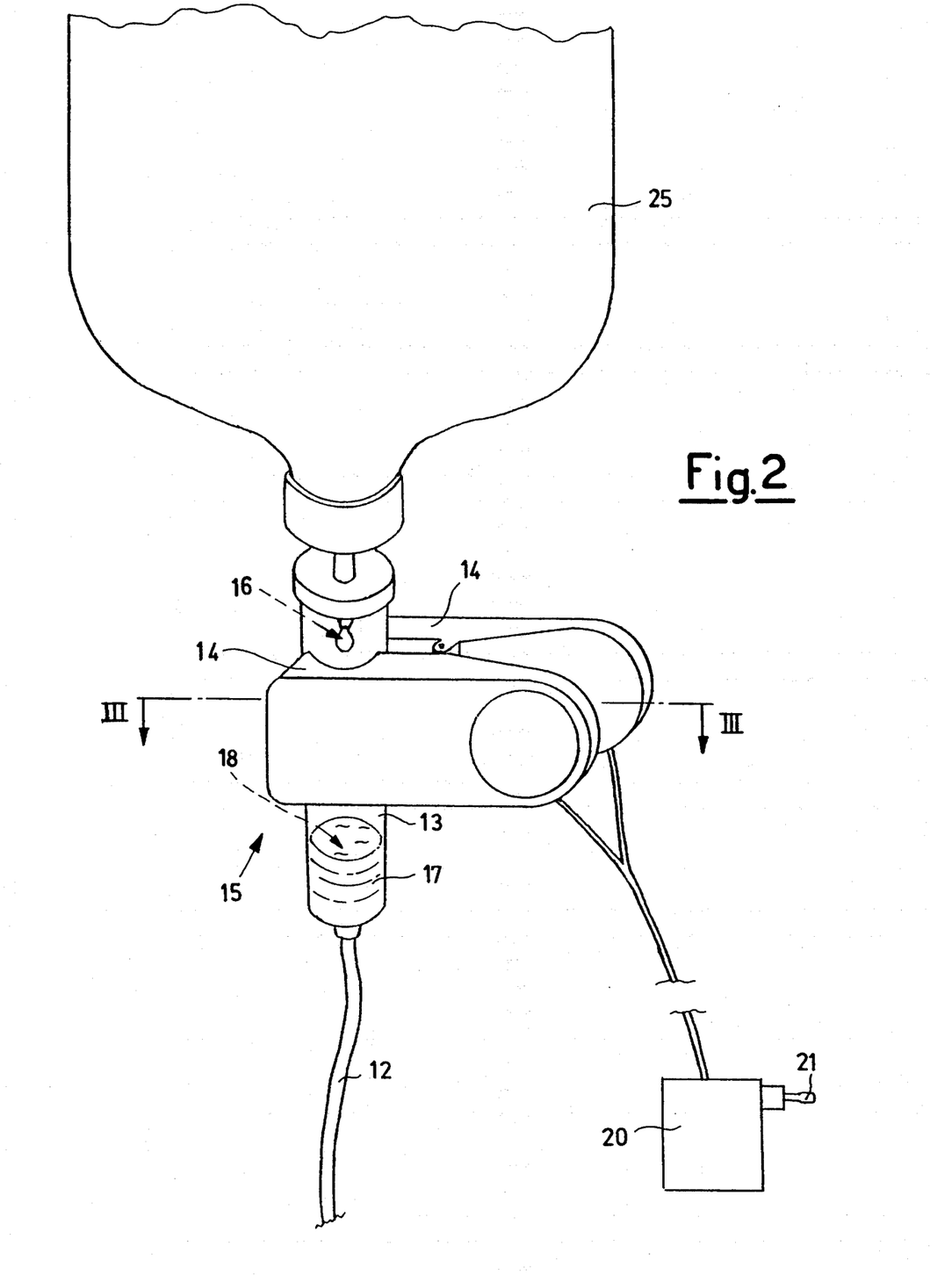
FIG. 2 shows the device of FIG. 1 applied to an intravenous infusion system.
Figure 3:
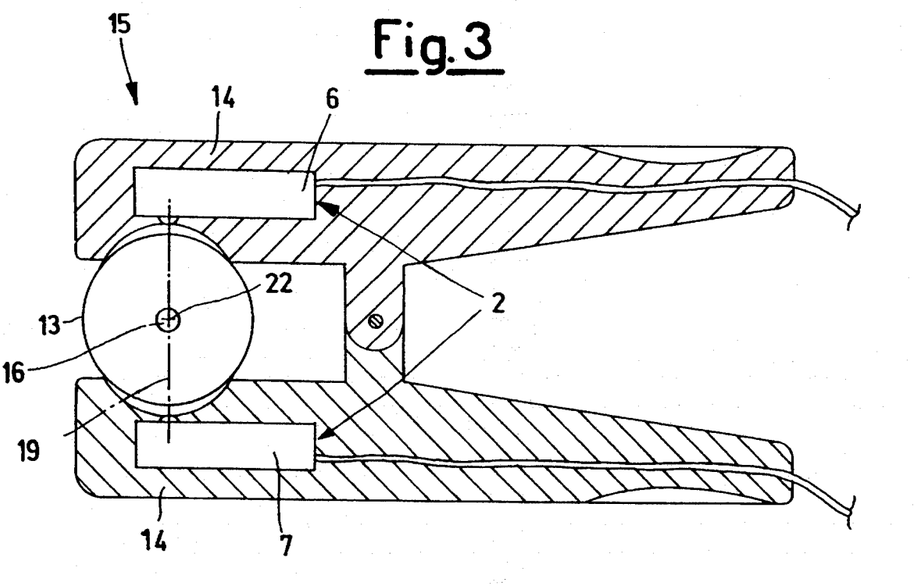
FIG. 3 is a section on the line III—III of FIG. 2.

The devices provided with optical sensors shown in FIGS. 2 and 3 operate regularly provided that an axis 22 of the droplet trajectory encounters the axis 19, i,e., that the droplet axis 16 passes through the axis 19. If this is not so, then the passage of the droplet 16 is not detected. This situation can occur for example if, due to an error in its application to the bottle 25, the axis of symmetry of the drip chamber 13 does not coincide with but instead cuts the axis 22. This occurs in practice if the bottle 25 and/or reservoir 13 are very inclined instead of upright.

Under such conditions when the total time interval counted by the time interval measuring element 3 exceeds the predetermined, this activates the warning elements 8, 9 even though the intravenous infusion system is operating regularly.

In addition, if the device 1 is of the type which also comprises the valving element 11 there is an unjustified interruption in delivery because of the compressing of the tube 12.

Figure 4:
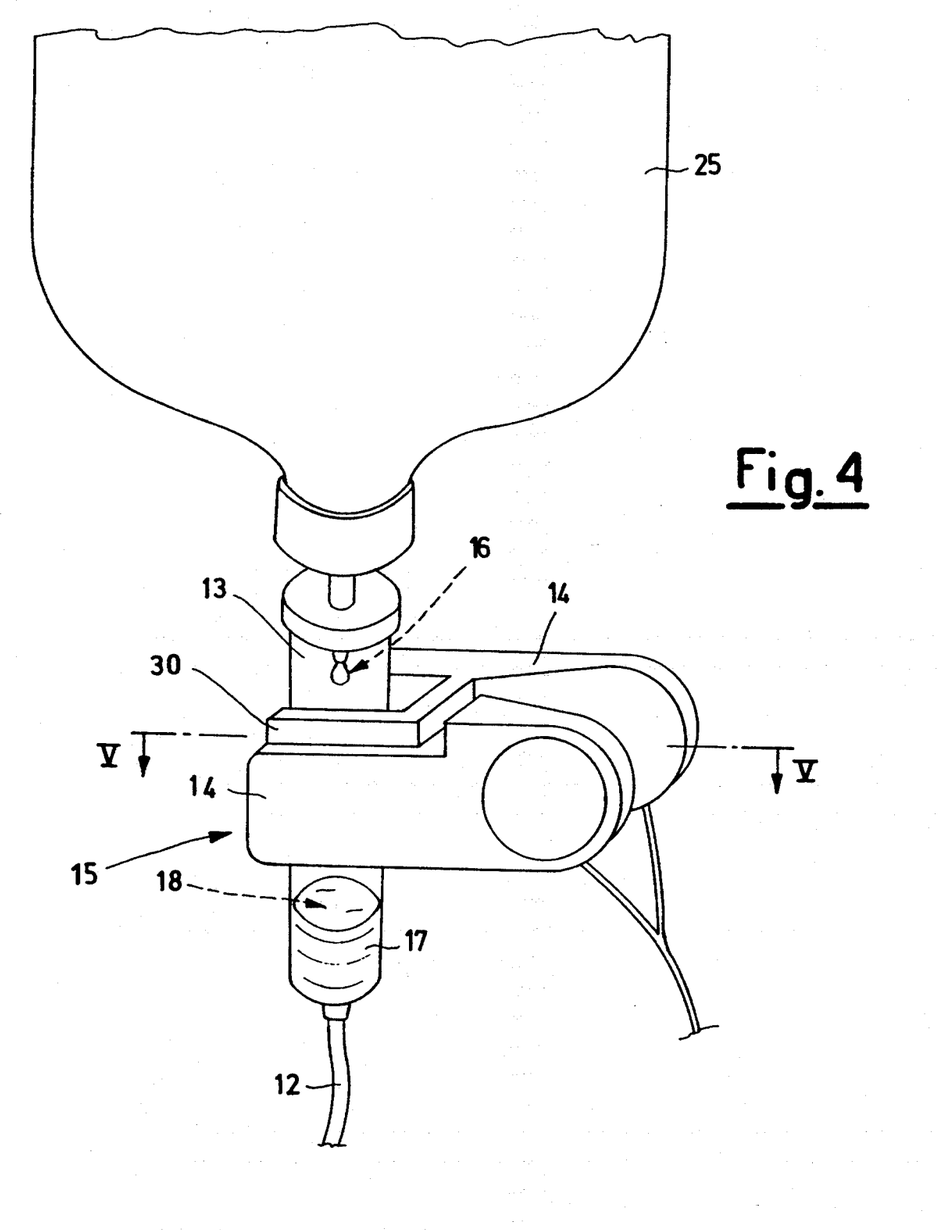
FIG. 4 is a perspective view of a second embodiment of the device according to the invention, which differs from that of FIGS. 1-3 by the structure of the gripper element and sensor element.
Figure 5:
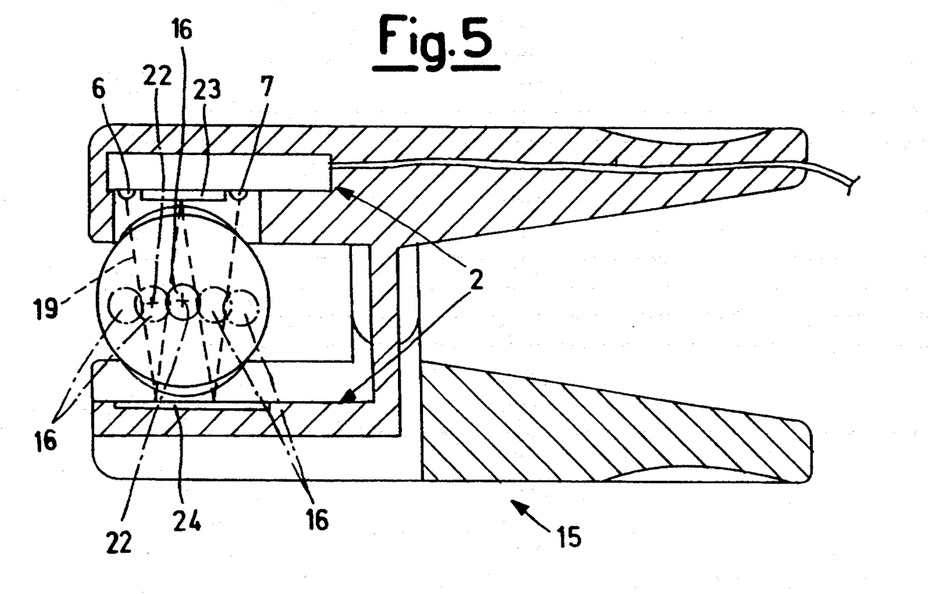
FIG. 5 is a section on the line V—V of FIG. 4.
Figure 6:
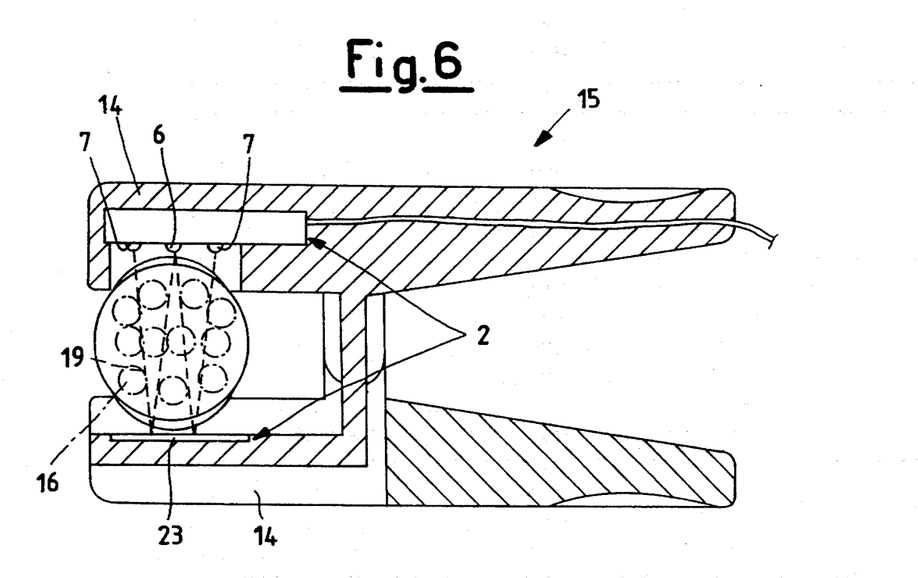
FIG. 6 is a section corresponding to that of FIG. 5 in which the device shown represents a third embodiment differing from that shown in FIG. 5 by the structure of the sensor element.
Figure 7:
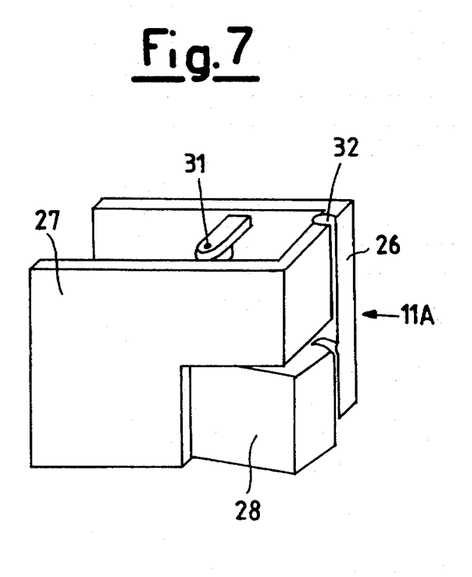
FIG. 7 is a front perspective view of a second embodiment of the valving element.
Figure 8:
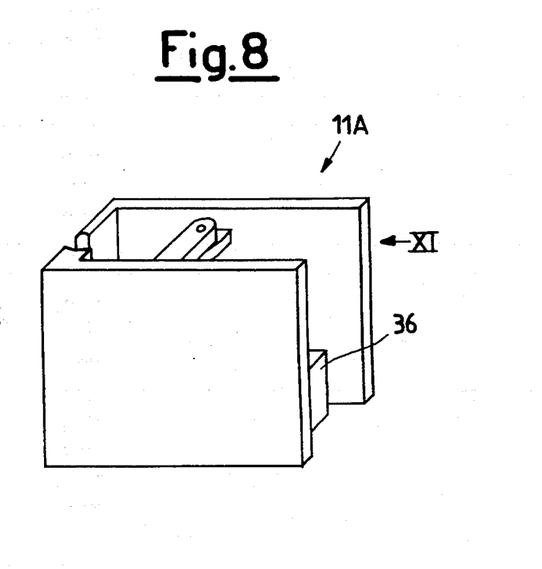
FIG. 8 is a rear perspective view of the valving element of FIG. 7.
Figure 9:
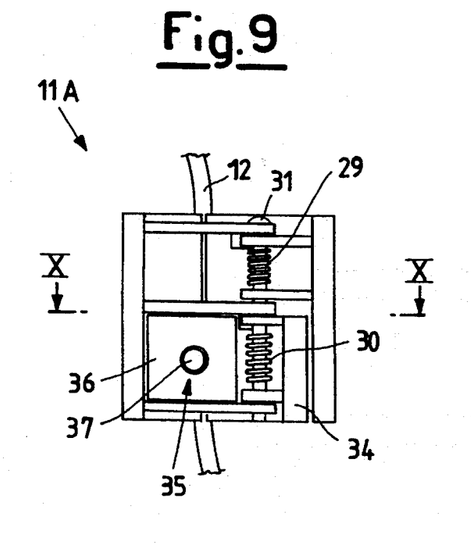
FIG. 9 is a view in the direction of the arrow IX of FIG. 8.
Figure 10:
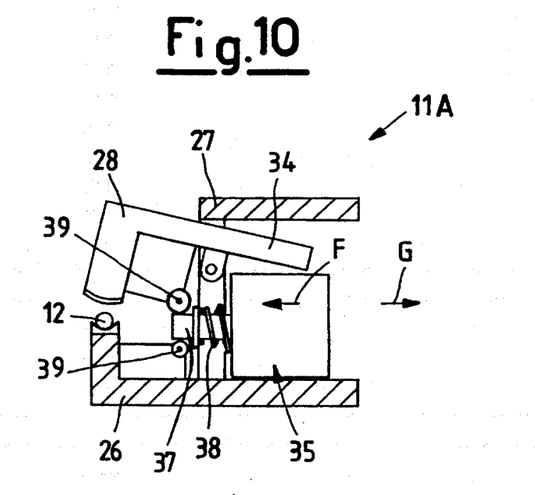
FIG. 10 is a section on the line X—X of FIG. 9.
Figure 11:
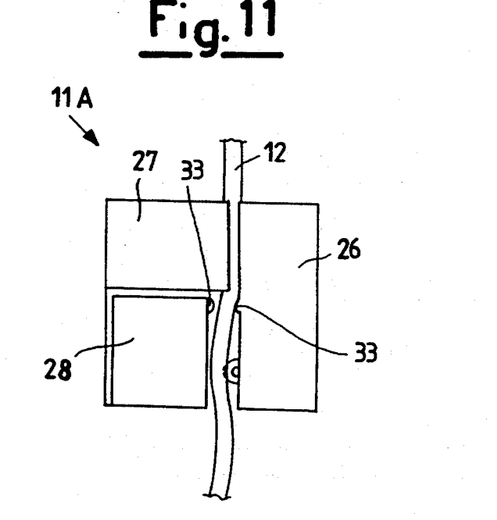
FIG. 11 is a front view of the valving element of FIG. 7 in the position in which it does not prevent flow.
Figure 12:
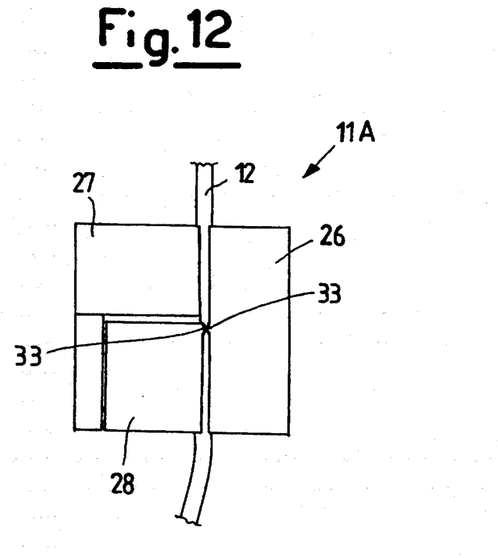
FIG. 12 is a front view of the valving element of FIG. 7 in the position in which it prevents flow.

This drawback can be overcome by the embodiments shown in FIGS. 4, 5 and 6. The device shown in FIGS. 4 and 5 comprises the transmitting portion 6, the receiving portion 7, a first reflex reflector 23 and a second reflex reflector The transmitting portion 6, the receiving portion 7 and the first reflex reflector 23 are all positioned on the same side of the axis 22 of the droplet trajectory, whereas the second reflex reflector 24 is positioned on the other side, on an appendix 30 (FIG. 4) fixed to the first jaw 14 of the gripper element 15. The reflex reflector 24 is positioned to form a constant reflection angle for the received ray, independently of the amount by which the two jaws 14 of the gripper 15 are opened.

The axis 19 becomes a broken polygonal line between the said elements, giving it maximum probability of encountering the droplet 16, independently of the axis of the trajectory 22 followed by the droplet.

This embodiment therefore operates regularly even if the axis of symmetry of the drip chamber 13 cuts the axis 22. In the illustrated embodiment the axis or broken polygonal line 19 comprises four parts because it undergoes three reflections. By choosing suitable reflex reflectors 23 and 24 it is however possible to increase or decrease the number of reflections and hence the number of component parts of the broken line 19, so that droplets of a particularly small diameter can also be detected. The embodiment shown in FIG. 6 uses photosensors and differs by comprising a transmitting potation 6 positioned between two side-by-side receiving portions 7 all opposing a first reflex reflector 23.

A second embodiment of a valving element 11A is Shown in FIGS. 7-12. From the operational viewpoint the second embodiment of the valuing element 11A differs from the first, shown in FIG. 1, in that in this second embodiment the valving element 11A is able to maintain the tube 12 closed without absorbing electrical energy. This is a great advantage in tens of practical use and construction because the device 1 can be made independent of the main supply and more easily miniaturized. In this respect, in its first embodiment the valving element 11 can compress the tube 12 only if the electromagnet is energized and hence only if electrical power is present, with a corresponding current consumption. This means that if the power supply is from an electric battery the shut-off state can be maintained only for a limited time period, which is further reduced because of the presence of further electricity-consuming components in the device.

In the second embodiment of the valving element or multiple gripping element 11A the electromagnet acts only in the sense of releasing a locking element which is able to compress the tube 12 by the effect of the action of elastic means which are preloaded on applying the monitoring device 1 to the intravenous infusion system. More specifically the second embodiment of the valving element 11A comprises a multiple gripper element of the normally closed type, indicated overall by 15 and comprising a first jaw 26, a second jaw 27 and a third jaw 28, a first spring 29, a second spring 30 and a locking device 35. The first jaw 26 operates against the second jaw 27 and the third jaw 28 by the action of the first spring 29 and the second spring 30 respectively, which operate side by side on a single pin 31. The first jaw 26 and second jaw 27 encounter each other to form a tubular groove 32 the diameter of which is such that it adheres to the tube 12 without compressing it or reducing its internal diameter, but such as to be able to keep the valuing element 11A retained on the tube 12. In contrast the first jaw 26 and third jaw 28 encounter each other with a profile such as to compress the tube 12.

In the illustrated embodiment both the first jaw 26 and third jaw 28 are provided with tube compressing projections 33 able to generate a high localized pressure on the tube 12, which being traditionally of flexible material is easily compressed by the elastic force of the second spring 30. As can be seen in particular in FIG. 10, the third jaw 28 comprises a stem 34 which extends parallel to, and inwards of, the corresponding stem of the second jaw 27. In this manner when acting on the first jaw 26 and in particular on the second jaw 27 in order to open them, the third jaw 28 is also urged into its open position. The third jaw 28 is then locked in its open position by the automatic action of the locking device 35, which comprises an electromagnet 36, a floating pin 37 and a third spring 8. The third spring 38 is preloaded such as to urge the pin 7, which is nothing other than the core of the electromagnet 36 (arrow F) between the first jaw 26 and the third jaw 28 so as to maintain them mutually open when the first jaw 26 and second jaw 27 are operated to open. The movement of the pin 37 between the first jaw 26 and third jaw 28 is preferably facilitated by two friction reducing rollers 9 when the electromagnet 36 acts in the sense of causing the pin 7 to move in the direction of the arrow G to release the third jaw 28.

Figure 13:
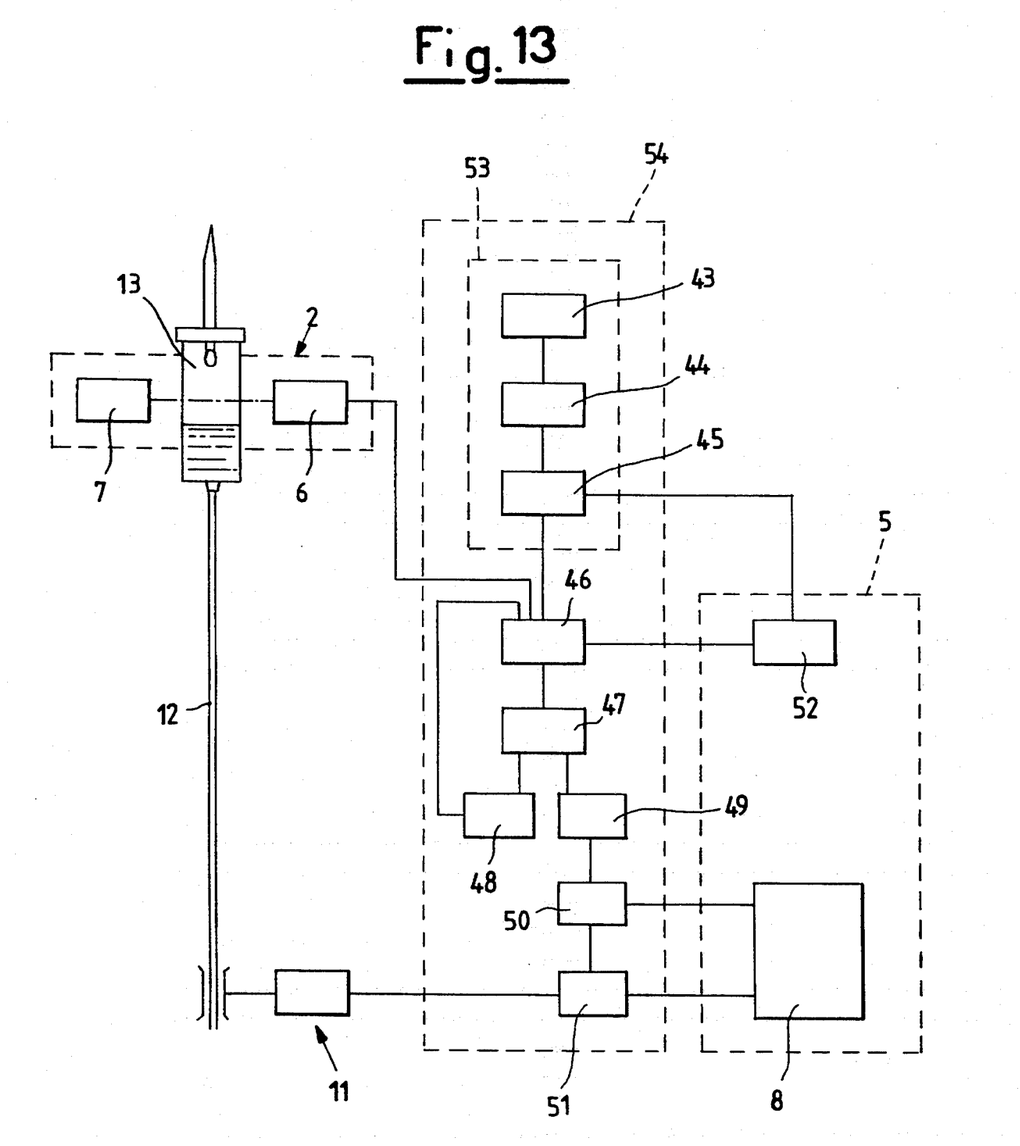
FIG. 13 is a schematic view of a fourth embodiment of the device according to the invention which differs from the first embodiment mainly by the structure of the electronic circuit, which is in the form of a second embodiment and represented by a second block diagram.
Figure 14:
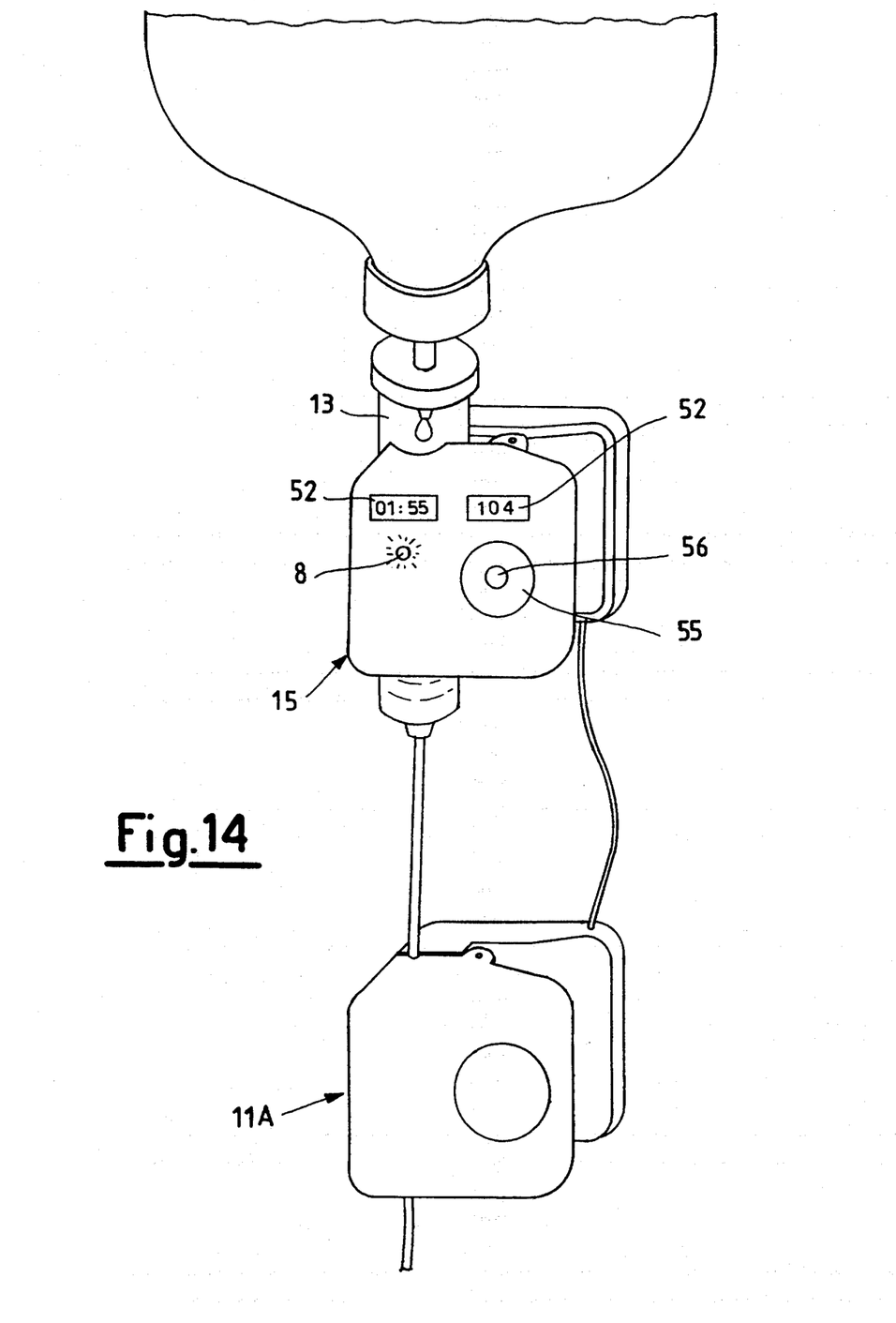
FIG. 14 is a perspective view of a device of the invention of the type provided with the valving element shown in FIGS. 7-12.

The operation of the multiple gripper element 15A is as follows. To apply the multiple gripper element 15A to the tube 12, the first jaw 26 and second jaw 27 are operated so as to open all three jaws 26-28, the third jaw 28 being simultaneously dragged into its open state by its engagement with the second jaw 27. The floating pin 37 becomes wedged between the first jaw 26 and third jaw 28 to maintain them mutually open. The multiple gripper element 15A is positioned so that the tube 12 lies between the jaws, and it is then left. The first jaw 26 and second jaw 27 adhere to the tube 12 at the tubular groove 32 without the tube being compressed, but such that the valve element 11A is retained. When the electromagnet 36 is energized the pin 37 moves in the direction of the arrow G, to hence close the third jaw 28 onto the first jaw 26, consequently compressing the tube 12 by the action of the second spring 30. With particular reference to FIG. 13, the device shown therein represents a third embodiment, which differs from the embodiment first mainly by the structure of the electronic circuit, which comprises the following units: an oscillator 43, a first droplet counter 44, a droplet frequency memory 45, a second droplet counter 46, a set frequency comparator 47, a first logic gate 48 and a second logic gate 49, a first threshold unit 50 and a second threshold unit 51, an acoustic/optical warning unit 8 and a luminous display 52. The units 43-45 form a self-setting unit 53. The units 43-51 can be physically combined into a single microprocessor 54, which can be housed in the gripper element 15A. FIG. 14 shows the luminous displays 52 and a warning light 8. The gripper element 15 comprises a recess 55 on which to press in order to open the element during its application to the drip chamber 13. Within the recess 55 there is the push-button 56 for switching on/switching off the monitoring device 1. In this manner, switching on and/or off are automatic on application and/or removal of the monitoring device 1 to or from the drip chamber 13 of the intravenous infusion system.

The operation of the monitoring device 1 is as follows. The monitoring device 1 must be applied to the intravenous infusion system when this has passed beyond its initial transient state and hence operates under normal working conditions with the correct delivery frequency. The electronic memory circuit initially memorizes said droplet delivery frequency and assumes it as the reference frequency. The delivery frequency should be the optimum as it has been chosen by specialized personnel operating the intravenous infusion system. The monitoring device 1 continuously compares the reference delivery frequency with the instantaneous frequency. If this latter is within a scheduled tolerance, which can be set during the setting-up of the system, the monitoring device 1 does not act. If not, then it indicates the abnormality by emitting light and/or acoustic signals, and finally possibly shutting off delivery by operating the valving element 11 or 11A if this is provided.

However, as will be apparent, in order for the described device to ensure proper administration, it is essential that the reference frequency is correctly established during the initial stages of administration by the person operating the intravenous infusion system. It is therefore apparent that even if an error arises in estimating the correct delivery frequency, this is assumed to be correct by the device 1 when this is applied to the chamber 13. The device 1 is therefore only able to check that the frequency is maintained within the prescribed frequency limits which have been assumed to be correct.

The device 1 of the fourth embodiment is therefore unable to safeguard the user against possible evaluation errors committed by the personnel responsible for its application. In other words, for its correct use it initially requires specialized personnel able to apply it correctly. This device therefore does not solve the problem in those cases in which for various reasons such personnel are not available, or in other words the device is unable to select the correct delivery frequency on the basis of the solution to be transfused to the patient.

Figure 15:
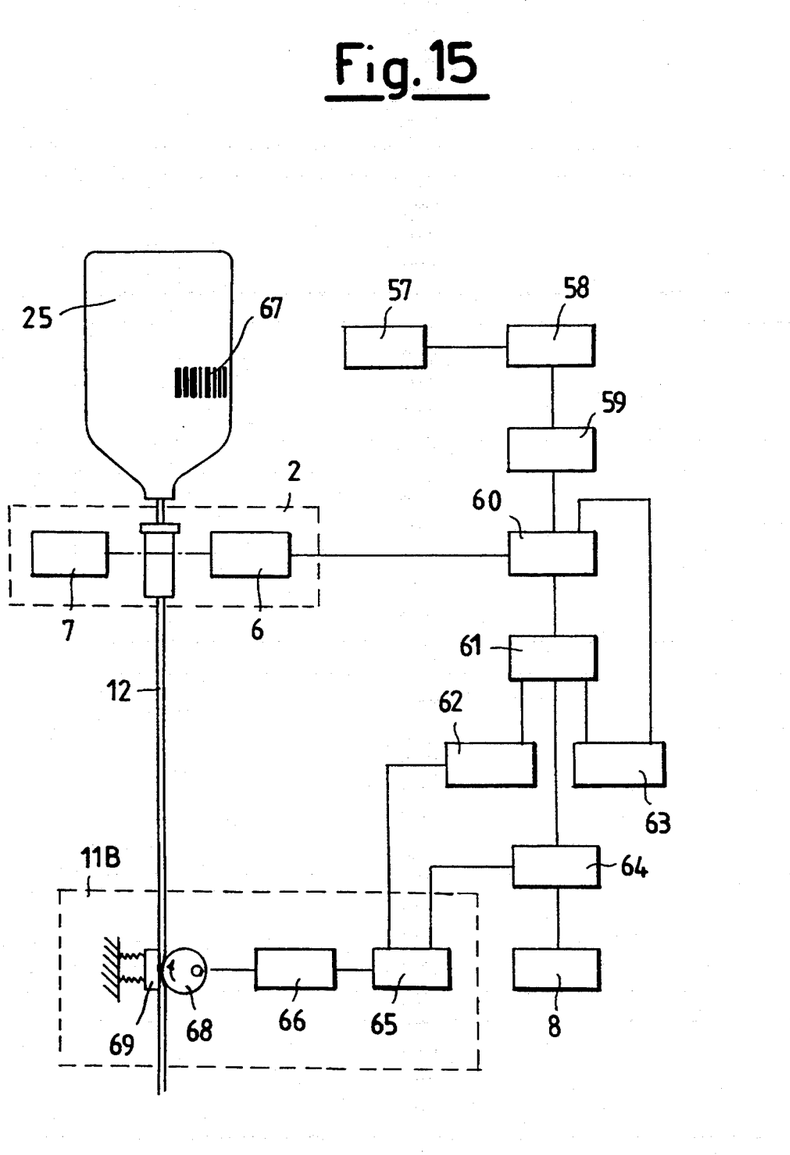
FIG. 15 is a schematic view of a fifth embodiment of the device which differs from the first and fourth embodiments both by the structure of the electronic circuit, which is in the form of a third embodiment and represented by a third block diagram, and by the structure of the valving element, which is formed as a third embodiment.

This drawback is obviated by the fifth embodiment of the device shown in FIG. 15. This device comprises substantially the following units: an optical reader 57, a data processor 58, an oscillator 59, a droplet counter 60, a comparator 61, a first 62, a second 63 and a third logic gate 64, the optical/acoustic warning unit 8, the valving element 11, the transmitting portion 6 and the receiving portion 7. The optical reading unit 57 is of the type able to read a code for example of bar type 67 applied to the bottle 25. The bar code 67 indicates the administration characteristics of the medicament and hence also its administration rate, which the circuit assumes as reference value by reading it by means of the unit 57.

The third embodiment (FIG. 15) of the valving element 11B comprises a unit 65 for the pulse control of a micromotor 66 which can be of the stepping or geared type, an eccentric roller or cam 68 and a counteracting member 69.

Figure 16:
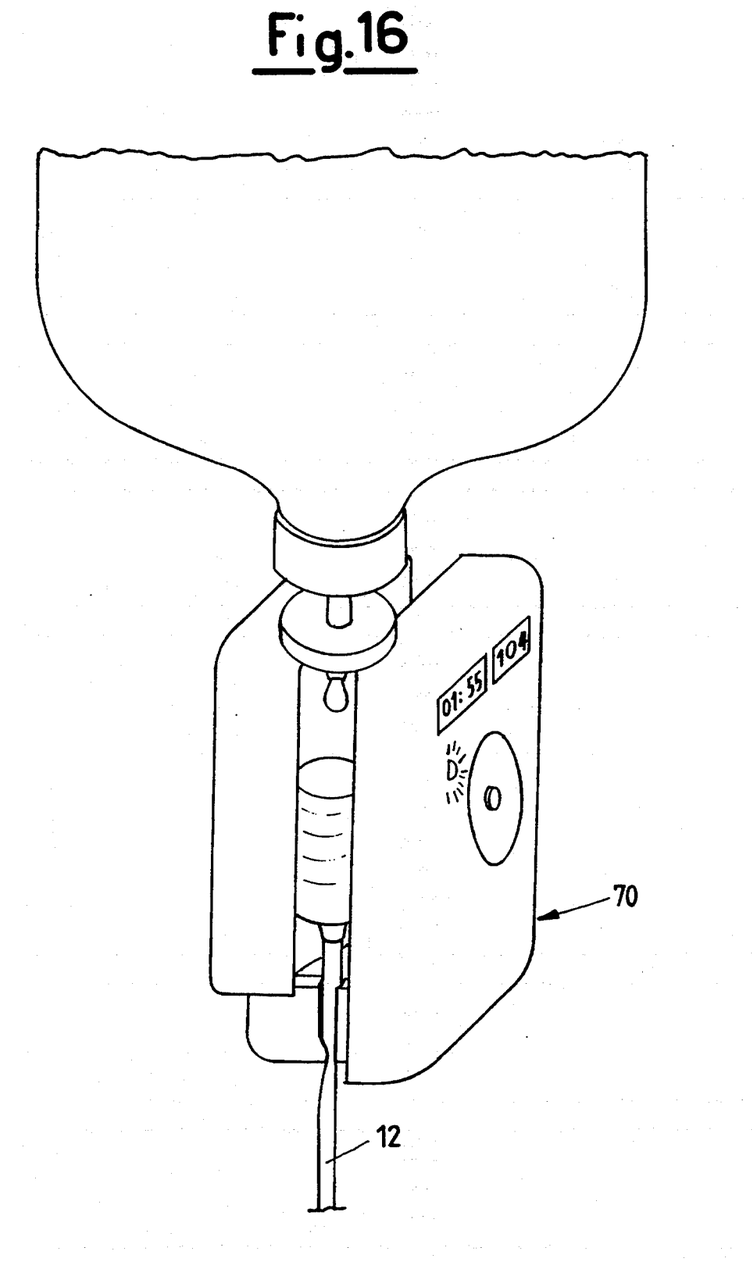
FIGS. 16 and 17 illustrate a sixth embodiment of the device, which differs from the preceding in that the sensor element, the electronic circuit and the valving element are combined into a single element.
Figure 17:
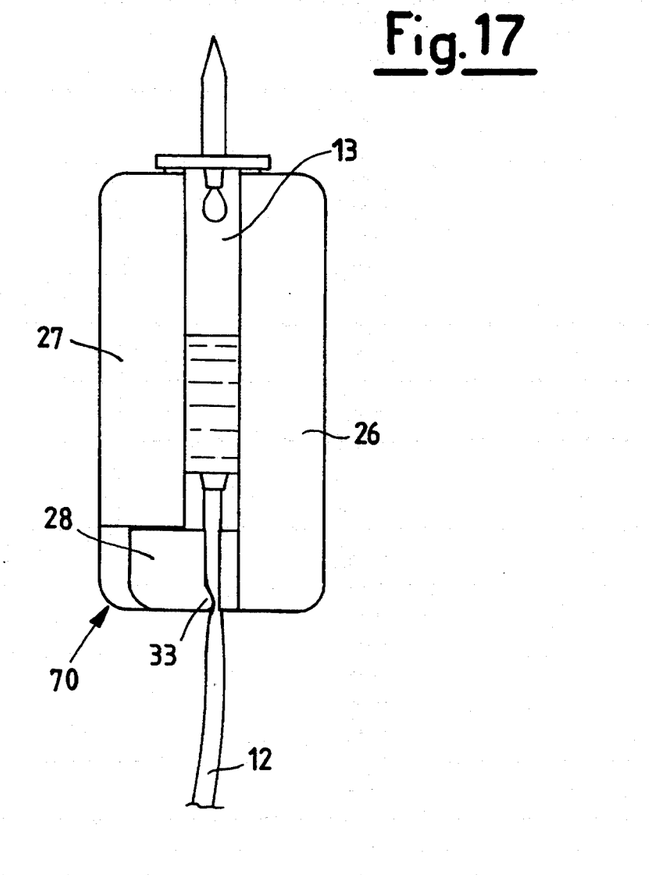

The embodiment of the device 1 shown in FIGS. 16 and 17 differs from the preceding in that the sensor element 2, the electronic circuit 54, 5 and the valving element 11 or 11A or 11B are combined into a single element 70 in which the upper part of the first jaw 26 and the second jaw 27 adhere to the drip chamber 13 instead of to the tube 12. The lower part of the first jaw 26 and the third jaw 28 are shaped to adhere to the tube 12 and be able to compress it.

Figure 18:
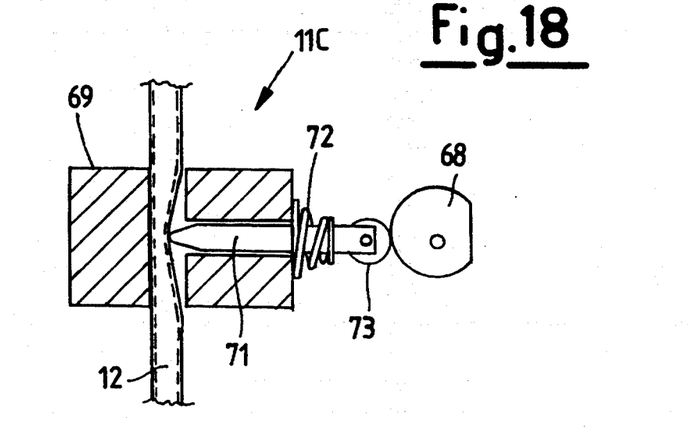
FIG. 18 shows a fourth embodiment of the valving element, which differs from the preceding in that the cam does not act directly on the tube.

The fourth embodiment (FIG. 18) of the valving element 11C has a more evolved structure. The eccentric roller or cam 68 compresses or slackens the tube 12 against the counteracting member 69, either directly or via an interposed plunger 71 with a wedge-shaped end opposed by a spring 72 and facilitated by a roller 73 (FIG. 18). The more the tube 12 is compressed the slower the flow of transfusion liquid.

The tube 12 is closed when the cam 68 is in the position giving maximum compression of the tube 12.

During operation, the position of the cam 68 and hence the delivery frequency are controlled by the electronic circuit of the monitoring device 1 on the basis of the administration frequency indicated by the bar code 67.

Any abnormality is indicated by the warning unit 8 or in the limit is eliminated by the stoppage of delivery determined by the cam 68.

In addition to operating in the initial and final stages, the geared motor 66 operates only for adjusting the delivery frequency, its electricity consumption therefore being very low. Hence the system can also be battery-powered in this case, with considerable advantages especially when moving the patient within the hospital.

The automatic appraisal of the administration rate by reading the bar code, in accordance with the fifth embodiment, is also perfectly applicable to actual infusion pumps.

I claim:

1. A device for monitoring an intravenous infusion system comprising at least one drip chamber for receiving droplets of a liquid for intravenous infusion, a delivery tube connected to said chamber, sensing means operatively associated with said drip chamber for sensing dripping droplets, an electronic unit including means for memorizing a droplet frequency, a droplet counter for counting the droplets sensed by said sensing means, a comparator means for comparing the frequency of droplets counted by said droplet counter with said memorized droplet frequency, relay means operable by said comparator means when said comparator means detects a difference between the frequency of droplets counted by said counter and said memorized droplet frequency, means operable by said relay means for terminating the flow of liquid through said delivery tube, said liquid flow terminating means including first (26) and third (28) relatively movable jaw means for selectively clamping closed said delivery tube (12), second jaw means (27) movable relative to said first jaw means (26) for clamping engagement to an associated support (12 or 13), second biasing means (30) for normally biasing said first (26) and third (28) jaws toward a clamping position relative to said delivery tube (12), first biasing means (29) for normally biasing said first (26) and second (27) jaws toward a clamping position relative to an associated support (12 or 13) and preloading said second biasing means (30), means (37, 38) for relatively moving said first (26) and third (28) jaws to a nonclamping position relative to said delivery tube (12), and means (35) for disabling said moving means (37, 38) whereby said preloaded second biasing means (30) biases said first (26) and third (28) jaws relatively toward each other to said clamping position.

2. The intravenous infusion system monitoring device as defined in claim 1 wherein said sensing means includes photosensing means for sensing dripping droplets.

3. The intravenous infusion system monitoring device as defined in claim 1 wherein said sensing means includes photosensing means for sensing droplets dripping generally downwardly along a generally vertical axis.

4. The intravenous infusion system monitoring device as defined in claim 1 wherein said sensing means includes photosensing means for sensing droplets dripping generally downwardly along a generally vertical axis, said photosensing means including means for transmitting a beam through an area through which droplets drip downwardly along said generally vertical axis, said photosensing means further including means for receiving said beam, and reflecting means for reflecting said beam at least once to effect the passage of said beam through said area at least twice before being received by said receiving means thereby increasing the probability of droplet sensing particularly when offset from said generally vertical axis.

5. The intravenous infusion system monitoring device as defined in claim 2 wherein said vertical axis corresponds to the axis of said at least one drip chamber.

6. The intravenous infusion system monitoring device as defined in claim 2 wherein said beam transmitting means and said beam receiving means are positioned generally at one side of said area and said reflecting means is positioned substantially opposite said area one side.

7. The intravenous infusion system monitoring device as defined in claim 2 wherein said beam transmitting means and said beam receiving means are positioned generally at opposite sides of said area.

8. The intravenous infusion system monitoring device as defined in claim 2 wherein said beam transmitting means and said beam receiving means are positioned generally at opposite sides of said area, and said reflecting means are positioned generally at opposite sides of said area.

9. The intravenous infusion system monitoring device as defined in claim 2 including means for clamping said sensing means upon said drip chamber, said clamping means including a pair of clamping jaws, said clamping jaws being in opposing clamping relationship at opposite sides of said drip chamber, said photosensing means including means for transmitting a beam through said drip chamber through which droplets drip downwardly along a generally vertical axis of said drip chamber, said photosensing means further including means for receiving said beam, and reflecting means for reflecting said beam at least once to effect the passage of said beam through said drip chamber at least twice before being received by said receiving means thereby increasing the probability of droplet sensing particularly when offset from said generally vertical axis.

10. The intravenous infusion system monitoring device as defined in claim 9 wherein said beam transmitting means and said beam receiving means are positioned on one of said clamping arms, and said reflecting means is positioned on another of said clamping arms.

11. The intravenous infusion system monitoring device as defined in claim 9 wherein said beam transmitting means and said beam receiving means are positioned generally on different ones of said clamping arms.

12. The intravenous infusion system monitoring device as defined in claim 9 wherein said beam transmitting means and said beam receiving means are positioned generally on different ones of said clamping arms, and said reflecting means are positioned on each of said clamping arms.

13. The intravenous infusion system monitoring device as defined in claim 1 wherein said disabling means includes electromagnet means which when briefly energized disables said moving means for effecting the relative movement of said first and third jaws through the bias of said preloaded second biasing means.

14. The intravenous infusion system monitoring device as defined in claim 13 wherein said sensing means includes photosensing means for sensing dripping droplets.

15. The intravenous infusion system monitoring device as defined in claim 13 wherein said sensing means includes photosensing means for sensing droplets dripping generally downwardly along a generally vertical axis.

16. The intravenous infusion system monitoring device as defined in claim 13 wherein said sensing means includes photosensing means for sensing droplets dripping generally downwardly along a generally vertical axis, said photosensing means including means for transmitting a beam through an area through which droplets drip downwardly along said generally vertical axis, said photosensing means further including means for receiving said beam, and reflecting means for reflecting said beam at least once to effect the passage of said beam through said area at least twice before being received by said receiving means thereby increasing the probability of droplet sensing particularly when offset from said generally vertical axis.

17. The intravenous infusion system monitoring device as defined in claim 13 wherein said vertical axis corresponds to the axis of said at least one drip chamber.

18. The intravenous infusion system monitoring device as defined in claim 13 wherein said beam transmitting means and said beam receiving means are positioned generally at one side of said area and said reflecting means is positioned substantially opposite said area one side.

19. The intravenous infusion system monitoring device as defined in claim 13 wherein said beam transmitting means and said beam receiving means are positioned generally at opposite sides of said area.

20. The intravenous infusion system monitoring device as defined in claim 13 wherein said beam transmitting means and said beam receiving means are positioned generally at opposite sides of said area, and said reflecting means are positioned generally at opposite sides of said area.

* * * * *